United States Patent [19]

Hermann et al.

[11] Patent Number: 5,527,326

[45] Date of Patent: Jun. 18, 1996

[54] VESSEL DEPOSIT SHEARING APPARATUS

[75] Inventors: George D. Hermann, Los Gatos; Kenneth H. Mollenauer, Santa Clara; Michelle Y. Monfort, Los Gatos, all of Calif.

[73] Assignee: Thomas J. Fogarty, Portola Valley, Calif.

[21] Appl. No.: 335,304

[22] Filed: Nov. 7, 1994

Related U.S. Application Data

[63] Continuation of Ser. No. 996,916, Dec. 29, 1992, abandoned.

[51] Int. Cl.$^6$ ............................ A61B 17/22; A61B 17/32
[52] U.S. Cl. ............................................. 606/159; 606/170
[58] Field of Search ..................................... 606/159, 170

[56] References Cited

U.S. PATENT DOCUMENTS

| | | |
|---|---|---|
| 3,320,957 | 5/1967 | Sokolik . |
| 3,749,085 | 7/1973 | Willson et al . |
| 3,799,172 | 3/1974 | Szpur . |
| 4,030,503 | 6/1977 | Clark, III ............................ 606/159 |
| 4,273,128 | 6/1981 | Lary ..................................... 606/159 |
| 4,682,607 | 7/1987 | Vaillancourt et al. .............. 128/772 |
| 4,706,671 | 11/1987 | Weinrib ............................. 606/159 |
| 4,808,163 | 2/1989 | Laub ................................... 604/105 |
| 4,890,611 | 1/1990 | Monfort et al. ..................... 606/159 |
| 4,909,781 | 3/1990 | Husted ................................ 606/159 |
| 4,926,858 | 5/1990 | Gifford, III et al. ................ 606/170 |
| 4,966,604 | 10/1990 | Reiss ................................... 606/170 |
| 4,979,939 | 12/1990 | Shiber ................................. 606/159 |
| 5,071,424 | 12/1991 | Reger .................................. 606/170 |
| 5,092,847 | 3/1992 | Pozzo .................................. 604/170 |
| 5,100,423 | 3/1992 | Fearnot ............................... 606/159 |
| 5,156,610 | 10/1992 | Reger .................................. 606/170 |

FOREIGN PATENT DOCUMENTS

| 4025799 | 2/1992 | Germany ............................ 606/170 |
|---|---|---|

OTHER PUBLICATIONS

Progress, an informational update from Cook Urological, Sept. 1991, cover and p. 7.
Product Package Label, Cat. No. GU 6359, Pfister–Schwartz Stone Retriever.
Reprint from Current Surgery, vol. 48, No. 2, Apr. 1991. *Surgical Technology*, New Techniques and Instrumentation for Management of Adherent Clot in Native and Synthetic Vessels; Thomas J. Fogarty et al.

*Primary Examiner*—Michael H. Thaler
*Assistant Examiner*—Nancy Mulcare
*Attorney, Agent, or Firm*—Limbach & Limbach; Charles P. Sammut

[57] ABSTRACT

An apparatus formed of a flexible coil concentrically disposed around a flexible wire includes one or more radially expansible, helically configured wire loops. The loops grip deposits within a vessel and allow the deposits to be sheared from the interior wall of the vessel when the apparatus is withdrawn from within the vessel.

15 Claims, 5 Drawing Sheets

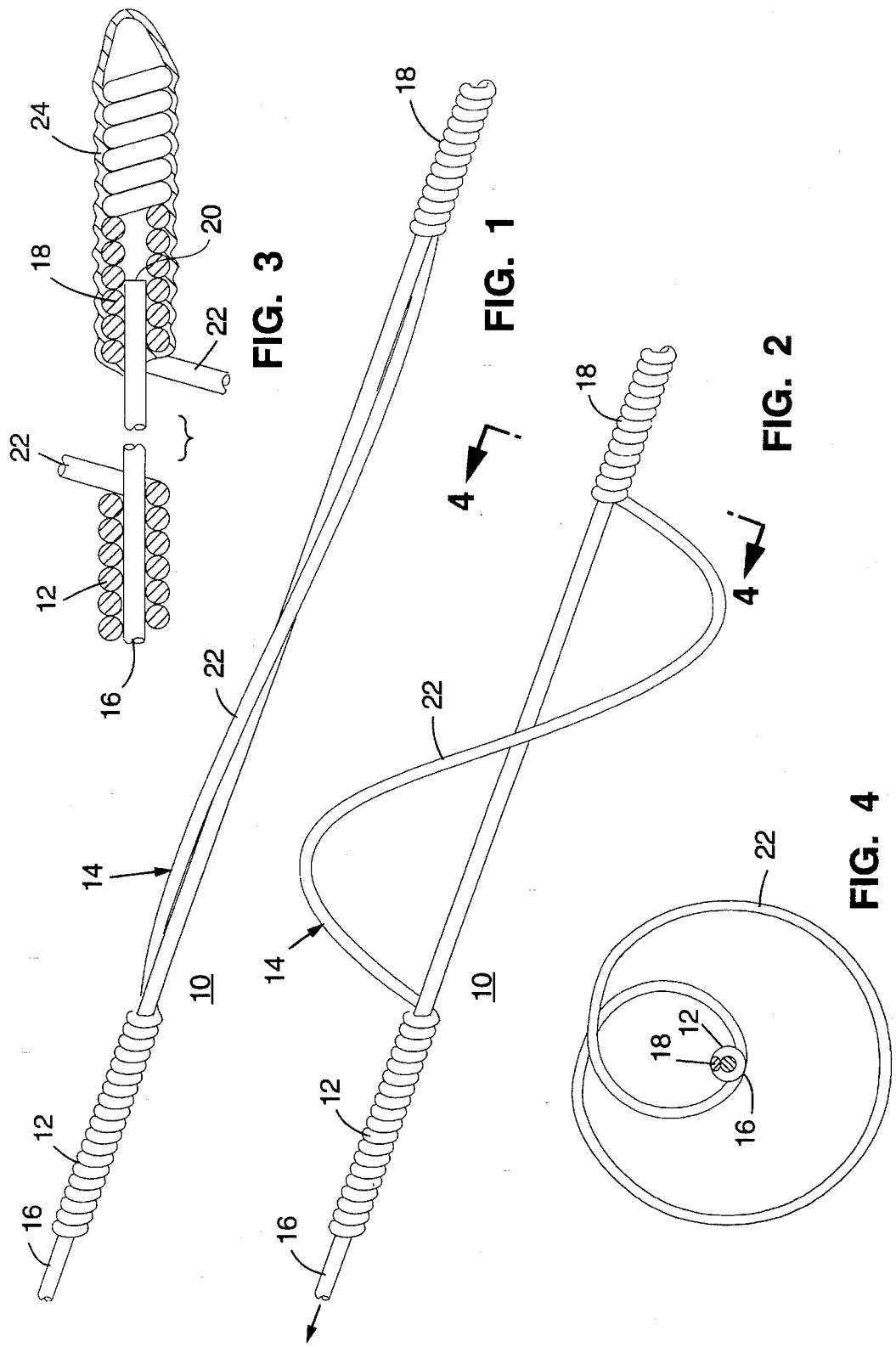

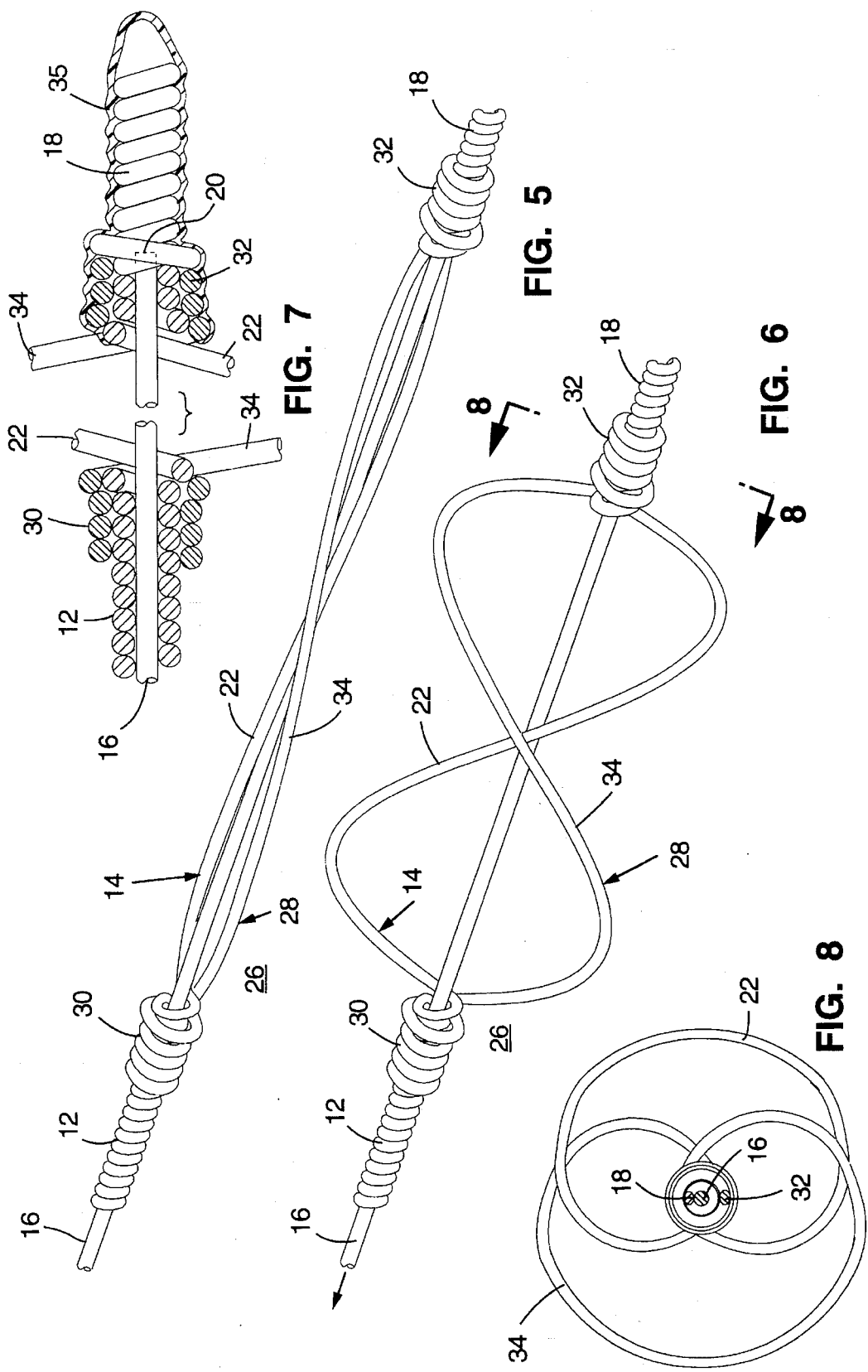

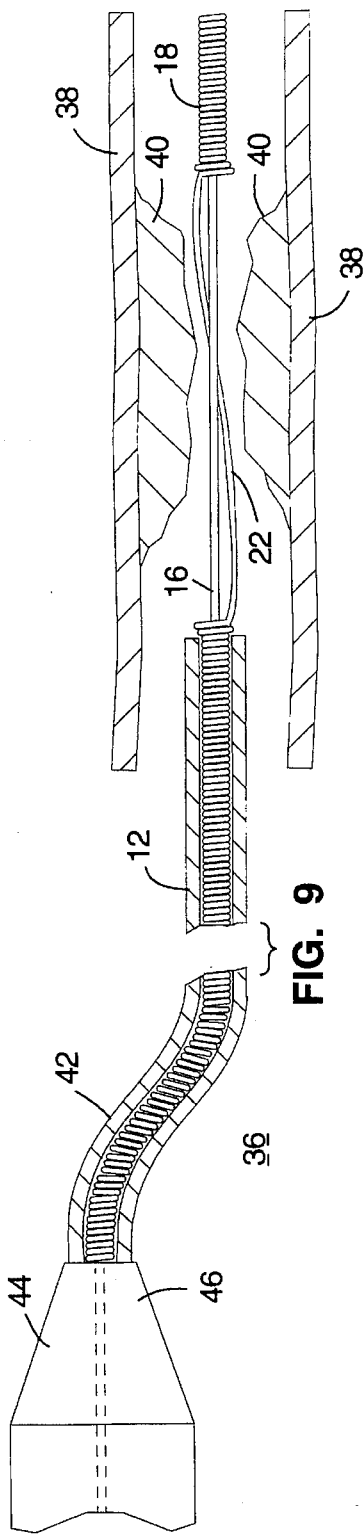
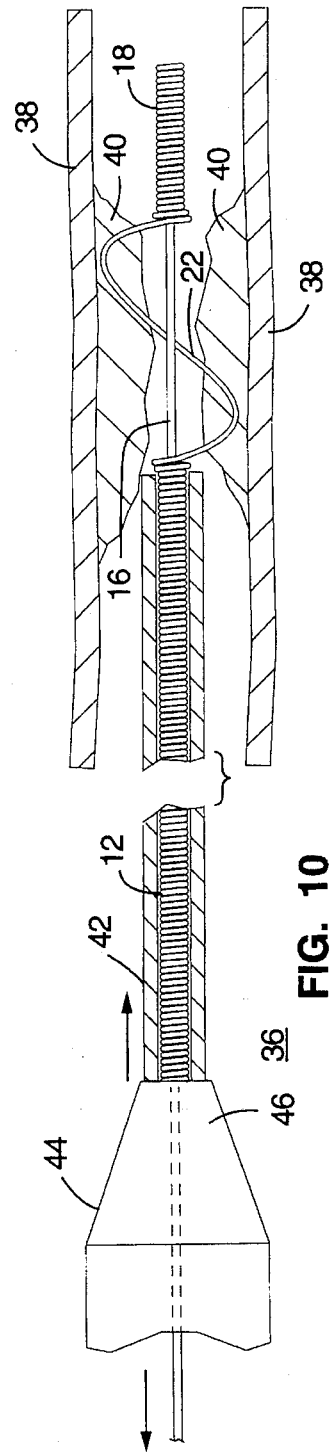
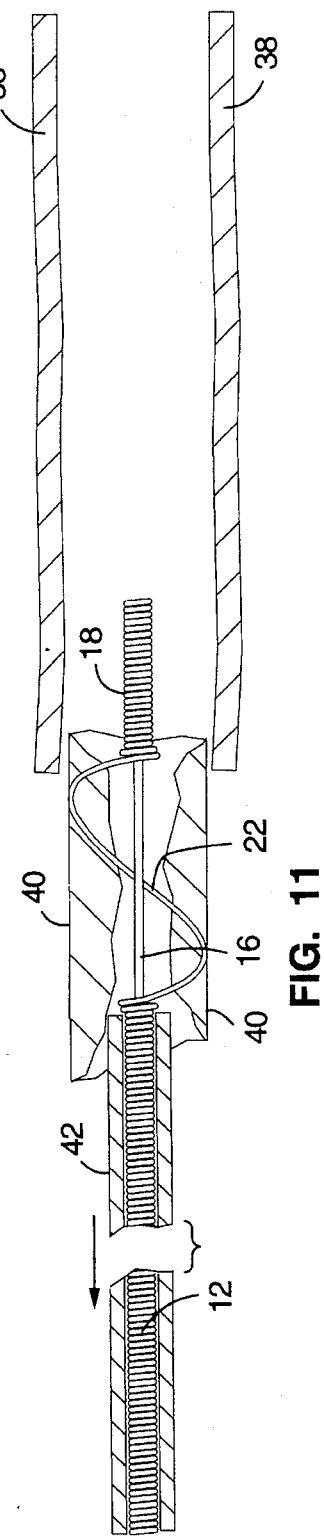
FIG. 9
FIG. 10
FIG. 11

VESSEL DEPOSIT SHEARING APPARATUS

This is a continuation of application Ser. No. 07/996,916 filed on Dec. 29, 1992, now abandoned.

BACKGROUND OF THE INVENTION

This invention relates to an apparatus for shearing deposits adhered to the interior wall of a vessel, for example an arteriosclerotic deposit from either a lumen of an occluded artery, a graft or a vascular conduit.

The removal of deposits from the interior of a vessel has been the object of much medical research. Such removal has been achieved by cutting or stripping. Alternatively the deposit may be compacted and simply left within a vessel such as an artery. In this regard see U.S. Pat. Nos. 4,452,244; 4,574,781; and 4,630,609. U.S. Pat. No. 4,890,611, assigned to the assignee of the present invention, discloses a method and apparatus which utilizes radially expansible helically configured wire loops to grip and shear arteriosclerotic deposits from the lumen of an occluded artery. The apparatus disclosed in this patent however, is complicated in that it requires a separate connection between its wire loops and their carrier.

SUMMARY OF THE INVENTION

The present invention is directed toward an apparatus wherein a flexible coil is concentrically disposed about a flexible wire to thereby provide a flexible yet relatively incompressible structure which can be inserted into a vessel, such as an artery, to grip a deposit, cause the deposit to be sheared and then remove the deposit from the vessel. A further object of this invention is to provide an apparatus where a radially expansible helically configured wire loop is part of a continuous flexible coil wound about a flexible wire which is inserted into a vessel. An additional object of this invention is to provide an apparatus which includes a second radially expansible helically configured wire loop which can either freely rotate about the flexible wire, with the first radially expansible helically configured wire loop acting as a stop, or may be fixedly positioned at desired angle with respect to the first radially expansible helically configured wire loop. Another object of this invention is to provide an apparatus having a structure which does not require a separate connection between the radially expansible helically configured wire loops and their carrier.

Other objects and aims of the invention will become clear upon a further reading of the disclosure and the claims.

BRIEF DESCRIPTION OF THE DRAWING

FIG. 1 is a partial perspective view of one embodiment of the invention with the gripping loop shown in a radially contracted state.

FIG. 2 is a perspective view of the apparatus shown in FIG. 1 with the gripping loop shown in a radially expanded state.

FIG. 3 is a fragmentary cross-sectional view of the apparatus shown in FIG. 2 showing a flexible covering encasing a portion of a flexible coil.

FIG. 4 is a cross-sectional view of the apparatus of FIG. 2 taken along line 4—4.

FIG. 5 is a partial perspective view of a second embodiment of the invention with the gripping loops radially contracted.

FIG. 6 is a perspective view of the embodiment shown in FIG. 5 with both of the gripping loops shown in a radially expanded state.

FIG. 7 is a fragmentary cross-sectional view of the apparatus of FIG. 6 illustrating the preferred orientation of the second gripping loop with respect to first gripping loop, and illustrating a flexible covering encasing a portion of a flexible coil.

FIG. 8 is a cross-sectional view of the apparatus of FIG. 6 taken along line 8—8 and including the flexible covering of FIG. 7.

FIG. 9 is a cross-sectional view of a clogged vessel having inserted within the vessel an embodiment of the invention which includes the apparatus of FIG. 1.

FIG. 10 is a cross-sectional view of the apparatus of FIG. 9 illustrating the gripping of a deposit within the vessel.

FIG. 11 is a cross-sectional view of the apparatus of FIG. 9 illustrating the removal of a sheared deposit from within a vessel.

DESCRIPTION OF THE PREFERRED EMBODIMENTS

Figure 12:
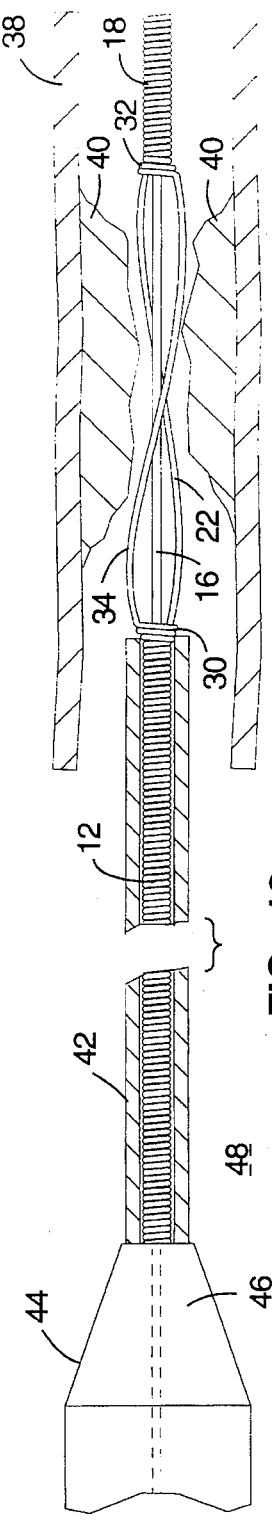
FIG. 12 is a cross-sectional view of a clogged vessel having inserted within the vessel an embodiment of the invention which includes the apparatus of FIG. 5.

With reference to FIGS. 1 through 15, elements common to each illustrated embodiment are referred to with the same reference numbers.

The First Embodiment

Referring now to FIG. 1, there is shown a portion of a first embodiment of a vessel deposit shearing apparatus 10 of the present invention. The vessel deposit shearing apparatus 10 includes a first region 12 of a flexible coil 14 which is concentrically disposed about a flexible wire 16 such that the individual loops within the region 12 are substantially in contact with each other. The first region 12 has an inner diameter slightly larger than the outer diameter of the flexible wire 16 to thereby allow the flexible wire 16 to freely slide through the first region 12. As will be apparent to those skilled in the art, when the flexible coil 14 is not curved or bent, the length of the region 12 is substantially equal to the product of the number of turns of the coil and the diameter of the wire used to form the flexible coil 14. Similarly, a second region 18 of the flexible coil 14 is concentrically disposed about a distal end 20 of the flexible wire 16. The second region 18 of the flexible coil 14 is fixedly mounted to the distal end 20 of the flexible wire 16 by any of a number of methods, such as soldering, bonding, heat shrinkage of the second region 18 about the wire 16. As shown in FIG. 3, in the preferred embodiment of the invention the distal end 20 only partially extends into the second region 18. This configuration allows the remainder of the second region 18 to flex more easily.

A third region 22 of the flexible coil 14 has a much lower pitch than that of the regions 12 and 18. As shown in FIG. 1 the third region 22 of the flexible coil is radially contracted about the flexible wire 16. Stated differently, the third region 22 in FIG. 1 is axially expanded about the axis of the flexible wire 16.

Referring now to FIG. 2, the second region 18 of the flexible coil 14 is secured to the distal end 20 of the flexible wire 16. As the flexible wire 16 is pulled through the first region 12 in a direction opposite to that of the distal end 20 (as depicted by the arrow line), the distance between the first region 12 and the second region 18 decreases thereby causing the third region 22 of the flexible coil to radially expand. Except as prevented by a hardened deposit within a vessel the average radius of the third region 22 increases inversely with the distance between the first region 12 and the second region 18. In the preferred embodiment of the invention the pitch of the third region 22 is selected to surround the wire 12 over a 360 degree angle. However, any desired angle may be selected, depending upon the gripping characteristics desired.

In the preferred embodiment of the invention the flexible coil 14 is made from 302 stainless steel spring wire having a diameter of either 0.012 inch or 0.014 inch. In addition, in the preferred embodiment of the invention, the wire 16 consist of stainless steel wire number 304 having a diameter either of 0.022 inch or 0.029 inch.

Referring now to FIG. 3, a relatively inert flexible coating or sheath 24 surrounds or encases both the second region 18 of the flexible coil 14 and the distal end 20 of the flexible wire 12. The flexible sheath 24 prevents friction, abrasion or unwanted cutting upon insertion of the apparatus 10 within a vessel such as an artery.

In the preferred embodiment of the invention, the sheath 24 is formed of a heat shrinkable polymer which is first placed over the second region 18 and reduced in size through the application of heat to that area. Alternatively, the second region 18 may be encased with a preformed cap having an inner diameter smaller than that of the second region 18 and a sufficient radial elasticity to stretch over the second region 18 and remain securely in place. As yet another alternative, the second region 18 may be dipped into a hot liquid polymer coating, which upon cooling, will adhere to both the second region 18 and the distal end 20. The flexible sheath 24 also serves to prevent longitudinal or axial expansion of the second region 18 when apparatus 10 is withdrawn from a vessel either with or without a gripped and sheared deposit.

FIG. 4 details the orientation of the third region 22 of the flexible coil 14 about the wire 16. Although FIG. 4 shows the third region 22 to be symmetrical about the flexible wire 16, it is not necessary that third region 22 be or remain symmetrical. In actual use, the third region 22 may deform unsymmetrically depending upon the shape and density of a deposit which is to be gripped and removed. In addition, the average radius of the third region 22 varies inversely, although not necessarily linearly, with the distance between the first region 12 and the second region 18. Because of the physical characteristics of the spring wire used to form the flexible spring 14, the third region 22 is expected to temporarily deform during use to thereby provide a more effective grip upon a deposit.

The Second Embodiment

In the embodiment shown in FIG. 5 a second flexible coil 28 includes a first region 30 which is concentrically disposed about the first region 12 of the flexible coil 14. The flexible coil 28 further includes a second region 32 which is concentrically disposed about second region 18 of the flexible coil 14. The second flexible coil 28 further includes a third region 34 (hereinafter also referred to as "gripping member 34") which connects the first region 30 to the second region 32.

The pitch of the third region 34, in the preferred embodiment of the invention, is selected to surround the wire 12 over a 360 degree angle.

Referring now to FIG. 6, when a force is applied to the wire 16 in a direction opposite to the distal end 20 (as depicted by the arrow lines), the distance between the first region 12 and the second region 18 decreases. Both the third region 22 of the flexible coil 14 and the third region 34 of the second flexible coil 28 radially expand.

As will be appreciated from FIG. 5, when the third region 22 of the flexible coil 14 and the third region 34 of the second flexible coil 28 are radially contracted, the third region 22 prevents the first region 30 and the second region 32 from sliding toward one another off either the first region 12 or the second region 18. Stated differently, when the third region 34 is axially expanded, the third region 22 acts as a stop for the regions 30 and 32.

In this second preferred embodiment of the invention, the first region 30 of the second flexible coil 28 and second region 32 of the second flexible coil 28 are affixed to the first region 12 and second region 18 of the coil 14, respectively. Such affixation is accomplished through soldering with a non-lead based material. Alternatively, such affixation may be accomplished through the use of a bonding agent such as a cyanoacrylate or through a suitably tensioned press fit between the region 12 and the region 30 and between the region 18 and the region 32. Furthermore, in the preferred embodiment of the invention the third region 34 of the second flexible coil 28 is oriented at about 180 degrees from the third region 22 of the flexible coil 14. However, depending upon the shape and placement of a deposit to be removed, it may be more desirable to orient these regions differently.

FIG. 7 further illustrates the orientation of the third region 22 with respect to the third region 34 in the vicinity of flexible wire 16. With this orientation, the third region 34 of the second flexible coil 28 prevents the uncoiling of the third region 22 of the flexible coil 14, and vice versa. As shown in FIG. 7, in the preferred embodiment of the invention, a sheath 35, similar to that of sheath 24 of FIG. 3, encases the regions 18 and 32 and the distal end 20.

FIG. 8 shows a cross-sectional view of the apparatus FIG. 6 and clearly illustrates the relative orientation of the third region 22 of the flexible coil 14 and the third region 34 of the flexible coil 28.

Operation

Referring now to FIG. 9 there is shown an apparatus 36 which has been inserted into a vessel 38, the vessel having an unwanted deposit 40. As will be evident from a comparison of FIGS. 1 and 9, the apparatus 36 includes the apparatus 10. In addition, a flexible covering or sheath 42 encases the first region 12 to thereby (1) reduce friction between the first region 12 and a vessel into which the apparatus 36 is inserted, and (2) to prevent the longitudinal or axial expansion of the first region 12 when force is applied to the first region 12 to withdraw the apparatus 36 from a vessel as explained and illustrated further herein.

It will be appreciated by those skilled in the art, that in order to insert the instrument 36 into a vessel such as an artery, the artery is prepared for treatment by making an incision (not shown) either proximal or distal to an unwanted deposit. After incision, the apparatus 36 is placed within the vessel 38 by introducing the distal end 20 of the apparatus 36 into the incision with the third region 22 (hereinafter also referred to as the "gripping member 22") in a radially contracted configuration. During insertion into the vessel 38, the entire apparatus 36 may be rotated axially to reduce the torquing force of the apparatus 28 on the vessel 38. Once a desired length of the deposit 40 has been traversed, the shearing member 22 is radially expanded by applying a force to the flexible wire 16, as shown in FIG. 10, in a direction opposite to the distal end 20 to thereby decrease the distance between the first region 12 and the second region 18. As will be explained further herein with reference to FIG. 15, a handle 44 is held, while a slidable knob pulls the flexible wire 16 in the direction indicated in FIG. 10.

In use, because of the ability of certain vessels such as arteries to expand without rupturing, it is sometimes desireable to radially expand the gripping member 22 beyond the normal radius of the vessel 38 to thereby create a greater shearing force against the deposit 40. When the gripping member 22 has adequately engaged the deposit 40, a physician pulls on the handle 44 which has a tapered end 46 securely attached to both the first region 12 and to the flexible sheath 42. As shown in FIG. 11, this force causes the deposit 40 to be pulled and thereby sheared from inside wall of the vessel 38. The sheared deposit 40 then moves along with the gripping member 22 as the apparatus 36 is withdrawn from the vessel.

In order to prevent a dislodged deposit 40 from escaping from gripping member 22, it is desirable to not allow the gripping member 22 to radially collapse until the deposit 40 has been successfully removed from within the vessel 38.

Figure 13:
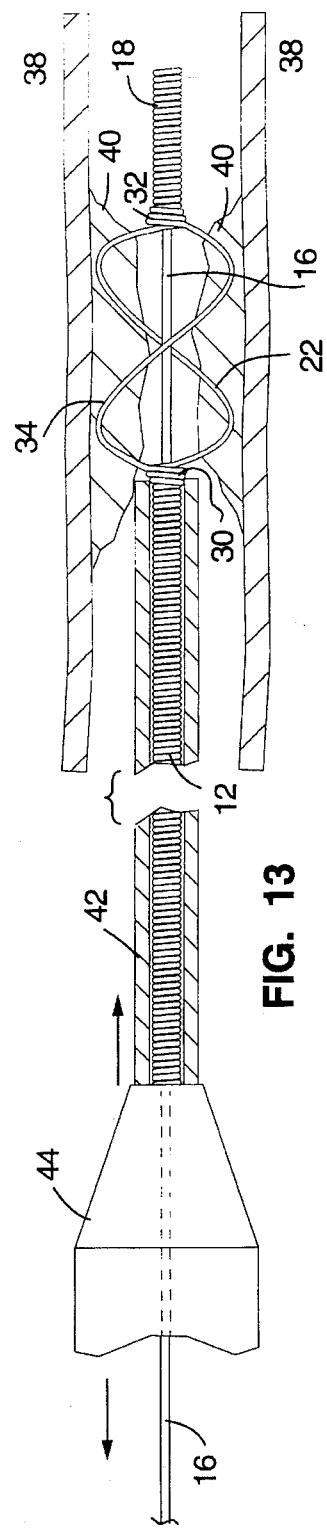
FIG. 13 is a cross-sectional view of the apparatus of FIG. 12 illustrating the gripping of a deposit within the vessel.
Figure 14:
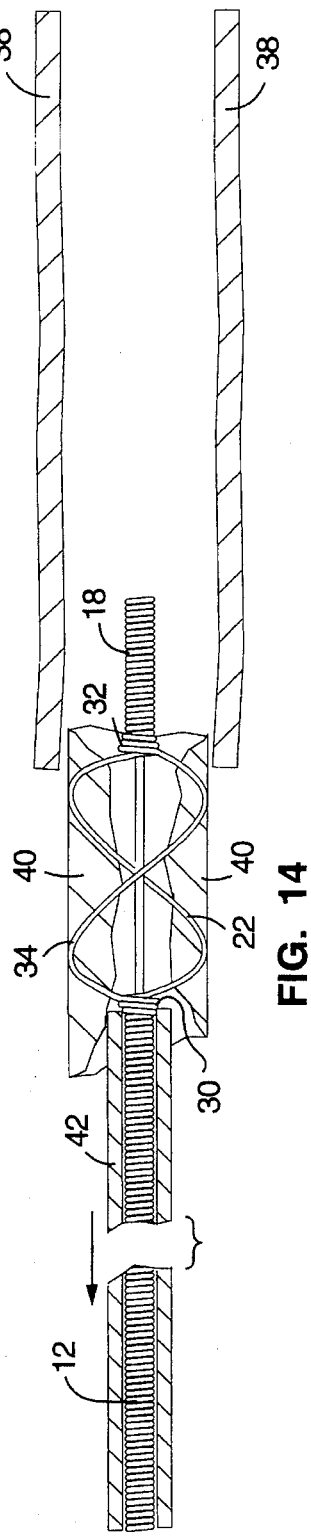
FIG. 14 is a cross-sectional view of the apparatus of FIG. 12 illustrating the removal of a sheared deposit from within the vessel.

Referring now to FIGS. 12, 13 and 14 an apparatus 48 is illustrated as an alternative embodiment to the apparatus 36 of FIGS. 9 and 10. In particular, the apparatus 48 incorporates the apparatus 26 shown in FIGS. 5 and 6. As explained with respect to the apparatus 36, once the apparatus 48 is inserted into a blocked vessel 38 and has traversed desired length of the deposit 40, both of the gripping members 22 and 34 are radially expanded by applying a force to the wire 16 opposite to the distal end 20 as shown in FIG. 13, to thereby decrease the distance between the first region 12 and the second region 18.

When a physician has determined by both feel and expertise that the deposit 40 has been adequately secured by the gripping members 22 and 34, the physician pulls on the handle 44 to thereby apply a force to the first region 12. This causes the deposit 40 to shear away from the inside walls of the vessel 38 and thereafter be transported together with gripping members 22 and 34 out of the vessel 38. The advantage of having a second gripping member 34 is the increased ability to grip a deposit and allow the application of a force sufficient to cause the deposit to shear from the interior wall of the vessel 38. In addition, because the second gripping member 34, is concentrically disposed in a direction opposite to that of the gripping member 22, the apparatus 48 is prevented from rotating away from the deposit 40 when the physician pulls on the apparatus 48. As will be appreciated by those skilled in the art, although two radially expandable gripping members are utilized in this embodiment of the invention, it is possible and may be desirable with certain types of deposits to have three or more radially expandable gripping members between the first region 12 and the second region 18.

Figure 15:
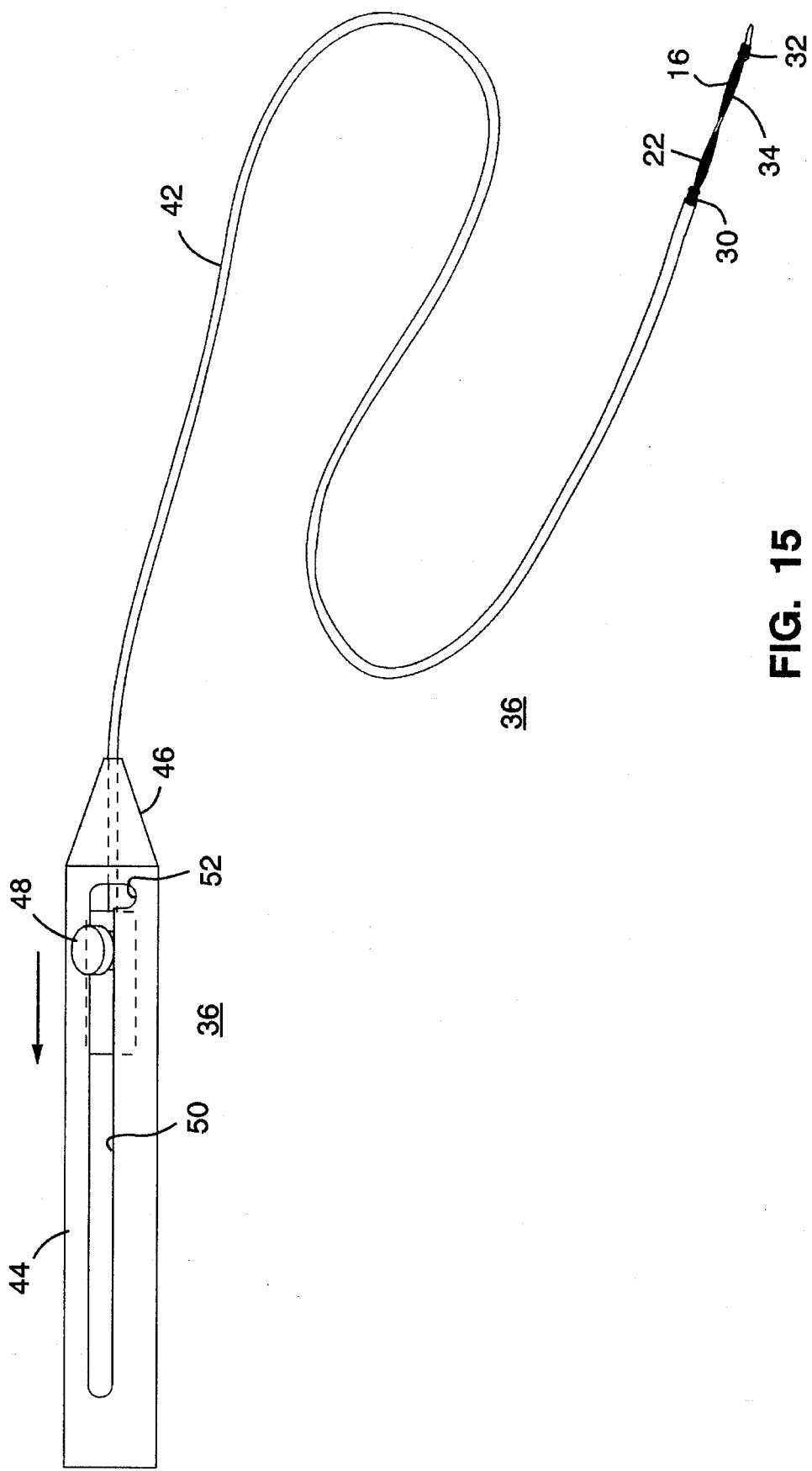
FIG. 15 is a perspective view of the embodiment shown in FIG. 9, illustrating further detail of the structure of the preferred embodiment of a handle.

Referring now to FIG. 15 there is shown preferred embodiment of a handle 44 which permits the one handed operation of the apparatus 48. In particular, the handle 44 includes the tapered end 46 which is fixedly attached to the flexible covering 42 and to the first region 12. The flexible wire 16 is attached to a slidable knob 49 which moves linearly along a slot 50. The slot 50 has at one end a notch 52, which allows a physician to lock the gripping member 22 in a radially collapsed position for insertion into a vessel. With the embodiment shown in FIG. 15, a physician controls both the insertion and withdrawal of the apparatus 36 and radial expansion and contraction of the gripping members 22 and 34 with one hand.

Although preferred embodiments of the invention have been illustrated and described, it should be understood that the invention is not intended to be limited to the specifics of such embodiments, but rather defined by the accompanying claims.

What is claimed is:

1. An apparatus for removing a deposit adhered to the interior of a vessel, the apparatus comprising:

a flexible wire having a proximal end and a distal end, the flexible wire having an outer diameter; and a continuous flexible coil concentrically disposed around the flexible wire, the coil having a first coiled region slidably received on a portion of the flexible wire, the first coiled region having an inner diameter sufficiently larger than the outer diameter of the flexible wire to allow the flexible wire to slide through the first coiled region, a second coiled region affixed to the distal end of the wire, and a third coiled region between the first region and the second region, the third coiled region having a pitch lower than that of the first and second regions, and having an average radius which varies inversely with the distance between the first coiled region and the second coiled region.

2. The apparatus of claim 1 further comprising:

flexible means affixed to the first coiled region of the continuous flexible coil operative to restrict axial expansion of the first coiled region.

3. The apparatus of claim 1 further comprising:

flexible means encasing the second coiled region of the continuous flexible coil.

4. The apparatus of claim 1 wherein said continuous flexible coil is formed of spring wire coiled about the flexible wire.

5. The apparatus of claim 4 wherein the axial length of the first coiled region of the continuous flexible coil is substantially equal to product of the number of turns of the continuous flexible coil within the first coiled region and the diameter of the spring wire.

6. The apparatus of claim 1 further comprising:

a knob attached to the proximal end of the flexible wire operative to adjust the distance between the first and second coiled regions of the continuous flexible coil.

7. The apparatus of claim 4 wherein the third coiled region comprises:

a helix disposed around the flexible wire.

8. An apparatus for removing a deposit adhered to the interior of a vessel, the apparatus comprising:

a flexible wire having a proximal end and a distal end, the flexible wire having an outer diameter;

a first continuous flexible coil concentrically disposed around the flexible wire, the first continuous flexible coil having a first coiled region slidably received on a portion of the flexible wire, the first coiled region having an inner diameter sufficiently larger than the outer diameter of the flexible wire to allow the flexible wire to slide through the first coiled region, a second coiled region fixedly attached to the distal end of the flexible wire, and a third coiled region between the first coiled region and the second coiled region, the third coiled region having a pitch lower than that of the first and second regions, and having an average radius which varies inversely with the distance between the first coiled region and the second coiled region; and a second continuous flexible coil having a first region, a second region, and a third region between the first and second regions, the first region of the second continuous flexible coil being disposed around at least a portion of the first coiled region of the first continuous flexible coil, the second region of the second continuous flexible coil being disposed around at least a portion of the second coiled region of the first continuous flexible coil, the third region of the second continuous flexible coil having an average radius which varies inversely with the distance between the first coiled region of the first continuous flexible coil and the second coiled region of the first continuous flexible coil.

9. The apparatus of claim 8 wherein the first region of the second continuous flexible coil is affixed to the first coiled region of the first continuous flexible coil.

10. The apparatus of claim 8 wherein the second region of the second flexible coil is affixed to the second coiled region of the first continuous flexible coil.

11. The apparatus of claim 8 wherein the third region of the second continuous flexible coil is positioned at an angle of 180° with respect to third coiled region of the first continuous flexible coil.

12. An apparatus for removing a deposit adhered to the interior of a vessel, the apparatus comprising:

a flexible wire having a proximal end and a distal end, the flexible wire having an outer diameter;

a first continuous flexible coil concentrically disposed around the flexible wire, the first continuous flexible coil having a first coiled region, a second coiled region and a third coiled region between the first and second coiled regions, the first coiled region of the first continuous flexible coil slidably received on a portion of the flexible wire having an inner diameter sufficiently larger than the outer diameter of the flexible wire to allow the flexible wire to slide through the first coiled region, the second coiled region of the first continuous flexible coil affixed to the distal end of the wire and the third coiled region of the first continuous flexible coil having a pitch lower than that of the first and second regions, and having an average radius which varies inversely with the distance between the first coiled region and the second coiled region;

a second continuous flexible coil having a first region, a second region and a third region between the first and second regions, the first region of the second continuous flexible coil being affixed to at least a portion of the first coiled region of the first continuous flexible coil, the second region of the second continuous flexible coil being affixed to at least a portion of the second coiled region of the first continuous flexible coil, the third region of the second continuous flexible coil having an average radius which varies inversely with the distance between the first coiled region of the first continuous flexible coil and the second coiled region of the first continuous flexible coil;

flexible means encasing at least a portion of the first coiled region of the first continuous flexible coil; and flexible means encasing at least a portion of the second coiled region of the first continuous flexible coil.

13. An apparatus for removing a deposit adhered to the interior of a vessel, the apparatus comprising:

a flexible wire having a proximal end and a distal end, the flexible wire having an outer diameter;

a continuous flexible coil concentrically disposed around the flexible wire, the coil having a first coiled region slidably received on a portion of the flexible wire, the first coiled region having an inner diameter sufficiently larger than the outer diameter of the flexible wire to allow the flexible wire to slide through the first coiled region, a second coiled region affixed to the distal end of the wire, and a third coiled region between the first coiled region and the second coiled region, the third coiled region having a pitch lower than that of the first and second coiled regions, and having an average radius which varies inversely with the distance between the first coiled region and the second coiled region; and a handle having an end and a slidable knob, the end fixedly attached to the first coiled region and the slidable knob attached to the flexible wire.

14. An apparatus for removing a deposit adhered to the interior of a vessel, the apparatus comprising:

a flexible wire having a proximal end and a distal end, the flexible wire having an outer diameter;

a first continuous flexible coil concentrically disposed around the flexible wire, the first continuous flexible coil having a first coiled region slidably received on a portion of the flexible wire, the first coiled region having an inner diameter sufficiently larger than the outer diameter of the flexible wire to allow the flexible wire to slide through the first coiled region, a second coiled region fixedly attached to the distal end of the flexible wire, and a third coiled region between the first coiled region and the second coiled region, the third coiled region having a pitch lower than that of the first and second coiled regions, and having an average radius which varies inversely with the distance between the first coiled region and the second coiled region;

a second continuous flexible coil having a first region, a second region, and a third region between the first and second regions, the first region of the second continuous flexible coil being disposed around at least a portion of the first coiled region of the first continuous flexible coil, the second region of the second continuous flexible coil being disposed around at least a portion of the second coiled region of the first continuous flexible coil, the third region of the second continuous flexible coil having an average radius which varies inversely with the distance between the first coiled region of the first continuous flexible coil and the second coiled region of the first continuous flexible coil; and a handle having an end and a slidable knob, the end fixedly attached to the first coiled region of the first continuous flexible coil and the slidable knob attached to the flexible wire.

15. An apparatus for removing a deposit adhered to the interior of a vessel, the apparatus comprising:

a flexible wire having a proximal end and a distal end, the flexible wire having an outer diameter;

a first continuous flexible coil concentrically disposed around the flexible wire, the first continuous flexible coil having a first coiled region, a second coiled region and a third coiled region between the first and second coiled regions, the first coiled region of the first continuous flexible coil slidably received on a portion of the flexible wire having an inner diameter sufficiently larger than the outer diameter of the flexible wire to allow the flexible wire to slide through the first coiled region, the second coiled region of the first continuous flexible coil affixed to the distal end of the wire and the third coiled region of the first continuous flexible coil having a pitch lower than that of the first and second regions, and having an average radius which varies inversely with the distance between the first coiled region and the second coiled region;

a second continuous flexible coil having a first region, a second region and a third region between the first and second regions, the first region of the second continuous flexible coil being affixed to at least a portion of the first coiled region of the first continuous flexible coil, the second region of the second continuous flexible coil being affixed to at least a portion of the second coiled region of the first continuous flexible coil, the third region of the second continuous flexible coil having an average radius which varies inversely with the distance between the first coiled region of the first continuous flexible coil and the second coiled region of the first continuous flexible coil;

flexible means encasing at least a portion of the first coiled region of the first continuous flexible coil;

flexible means encasing at least a portion of the second coiled region of the first continuous flexible coil; and a handle having an end and a slidable knob, the end fixedly attached to the first coiled region of the first continuous flexible coil and to the flexible means encasing at least a portion of the first coiled region of the first continuous flexible coil, and the slidable knob attached to the flexible wire.

* * * * *